United States Patent [19]

Livingston

[11] Patent Number: 5,303,592
[45] Date of Patent: Apr. 19, 1994

[54] METHOD AND APPARATUS FOR COILED TUBING INSPECTION

[76] Inventor: Waylon A. Livingston, 2250 Industrial Blvd., Norman, Okla. 73069

[21] Appl. No.: 802,536

[22] Filed: Dec. 5, 1991

[51] Int. Cl.$^5$ ............................................. G01N 29/22
[52] U.S. Cl. ........................................ 73/622; 73/151; 73/155
[58] Field of Search ........................... 73/151, 155, 622

[56] References Cited

U.S. PATENT DOCUMENTS

| | | | |
|---|---|---|---|
| 4,041,773 | 8/1977 | Hauldren et al. | 73/622 |
| 4,108,004 | 8/1978 | Murakami | 73/622 |
| 4,353,249 | 10/1982 | Lagus et al. | 73/155 |
| 4,404,853 | 9/1983 | Livingston | 73/622 |
| 4,475,399 | 10/1984 | Livingston | 73/622 |
| 4,487,072 | 12/1984 | Livingston | 73/622 |
| 4,541,064 | 9/1985 | Livingston | 364/552 |
| 4,794,791 | 1/1989 | Wittrisch | 73/151 |

*Primary Examiner*—Hezron E. Williams
*Assistant Examiner*—Rose M. Finley
*Attorney, Agent, or Firm*—Dougherty, Hessin, Beavers & Gilbert

[57] ABSTRACT

An inspection head for continuous acoustic energy inspection of coiled tubing consisting of a generally cylindrical test head for receiving the tubing longitudinally therethrough while being sealed on each end to maintain fluid couplant circulation. A cylindrical test array is disposed within the head to receive the tubing while directing a plurality of radially aligned compressional wave acoustic sensors and single in-line, angularly oriented shear wave acoustic sensors. Analysis of the various signal returns enables derivation of ovality, inside wall pitting, outside wall pitting, wall thickness, and transverse and/or longitudinal flaws.

31 Claims, 6 Drawing Sheets

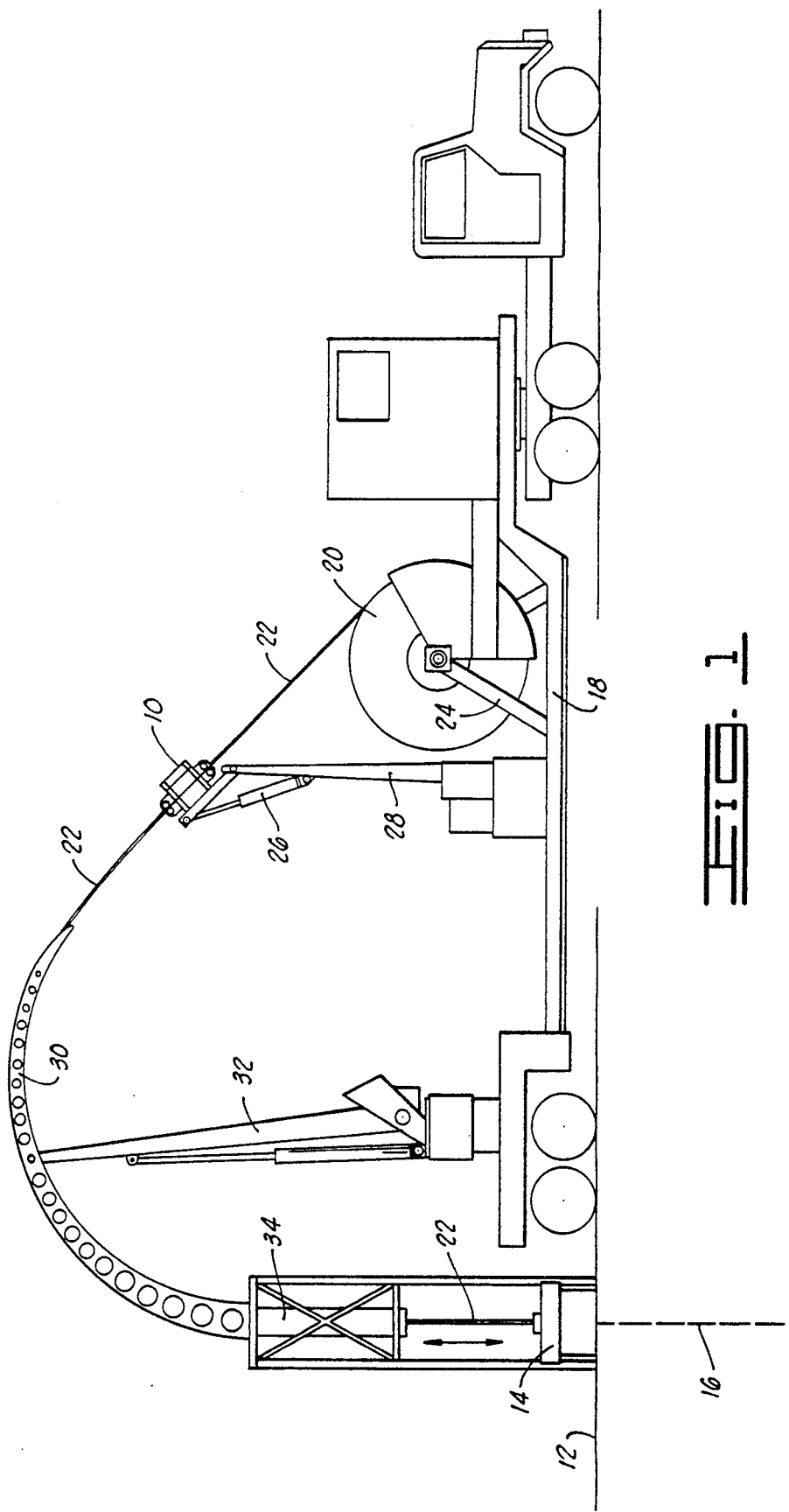

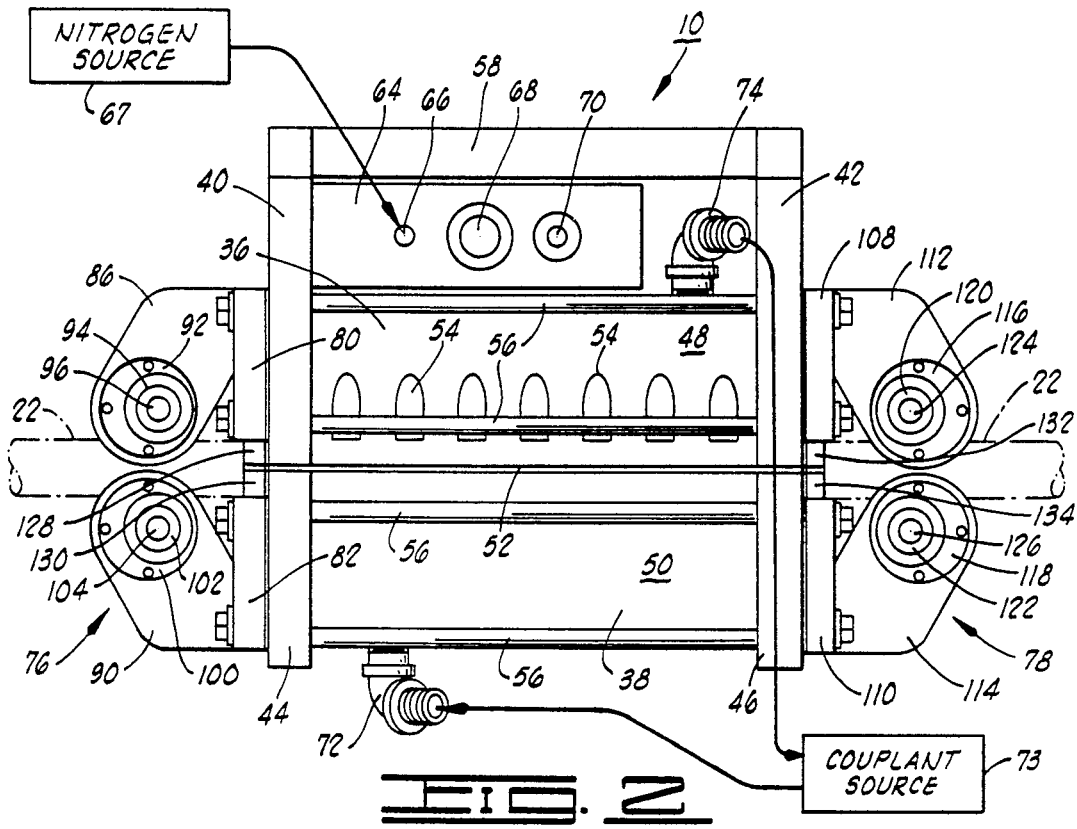
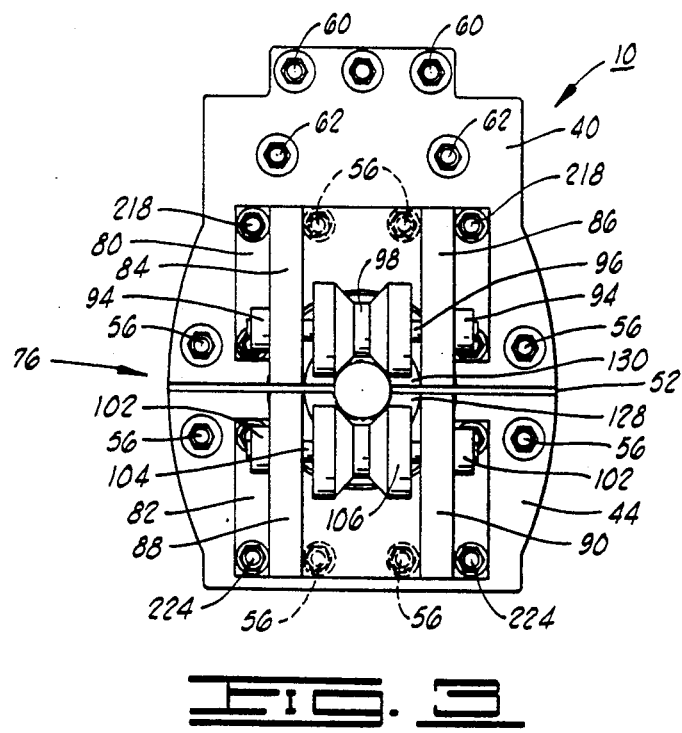

METHOD AND APPARATUS FOR COILED TUBING INSPECTION

BACKGROUND OF THE INVENTION

1. Field of the Invention

The present invention relates to sonic energy inspection of tubular goods and, more particularly, but not by way of limitation, it relates to a device for continuous testing of coiled steel tubing of the type used in the oil field.

2. Description of the Prior Art

To the inventor's knowledge, the present invention is the first apparatus of its type that is capable of continuous inspection of coiled steel tubing using an acoustic energy array. Several earlier patents in the name of the same inventor are considered to be within the prior art. U.S. Pat. No. 4,404,853 provides a method and apparatus for testing rigid steel drill pipe during use. That is, a sonic energy testing array is disposed in position at the rig floor to carry out defect detection in tubular goods such as oil well casing, drill pipe, tubing and the like. The device can also be utilized on pipe storage racks for testing of stored pipe or the like.

A variation on the basic device is the subject matter of U.S. Pat. No. 4,541,064 which discloses a particular form of acoustic energy array that is used for determining transverse and longitudinal defects as well as wall thickness defects. And the apparatus is specifically directed to signal processing circuitry and programmed sequence control computer. U.S. Pat. No. 4,475,399 is yet another patent directed to the signal processing circuitry that is utilized in the ultrasonic pipe testing system; and finally, U.S. Pat. No. 4,487,072 is directed to specifics of the electronic circuits utilized in carrying out the ultrasonic testing of tubular goods.

SUMMARY OF THE INVENTION

The present invention relates to method and apparatus for ultrasonic testing of continuous coiled tubing to make determinations as to remaining wall thickness, ovality of the tubing, and other related defects. The inspection head is installed about the coiled tubing in a location between the reel level-wind and the gooseneck that is characteristic of coiled tubing service rigs. The coiled tubing is directed by means of roller assemblies through the monitoring head which includes an internal space having the plural acoustic transducer array in position to receive the tubing therethrough. An acoustic energy couplant liquid is continually flowed through the monitor head in envelopment of the transducer array and tubing to maintain positive energy transfer, and pressurized nitrogen is circulated through all interior compartments having electronic circuit boards and bare wire connections. Basically, the transducer array includes eight ultrasonic transducers in circumferential array and aligned radially relative to the tubing axis. These transducers are sequentially pulsed repetitively. Two additional ultrasonic transducers are aligned on the array for the purpose of detecting surface pitting of the tubing.

Therefore, it is an object of the present invention to provide a testing device for determining the condition of coiled tubing continuously and at considerable throughput speeds.

It is also an object of the present invention to provide a coiled tubing inspection device that gives a continual indication of tubing ovality.

It is yet another object of the present invention to provide a device for testing tubular goods immediately adjacent to the wellhead during operational use.

It is also an object of the invention that it be reliable in operation to continually make precise determinations relative to coiled tubing.

Finally, it is an object of the present invention to provide a device for continuous monitoring of coiled tubing specifications as it is paid into or drawn out of the borehole.

Other objects and advantages of the invention will be evident from the following detailed description when read in conjunction with the accompanying drawings which illustrate the invention.

BRIEF DESCRIPTION OF THE DRAWINGS

FIG. 1 is an idealized illustration of a coiled tubing reel truck adjacent a well head with the tubing inspection device positioned for inspection of the coiled tubing;

FIG. 2 is a side view in elevation of the monitoring head assembly;

FIG. 3 is an end view in elevation of the monitoring head assembly;

DETAILED DESCRIPTION OF THE INVENTION

Figure 4:
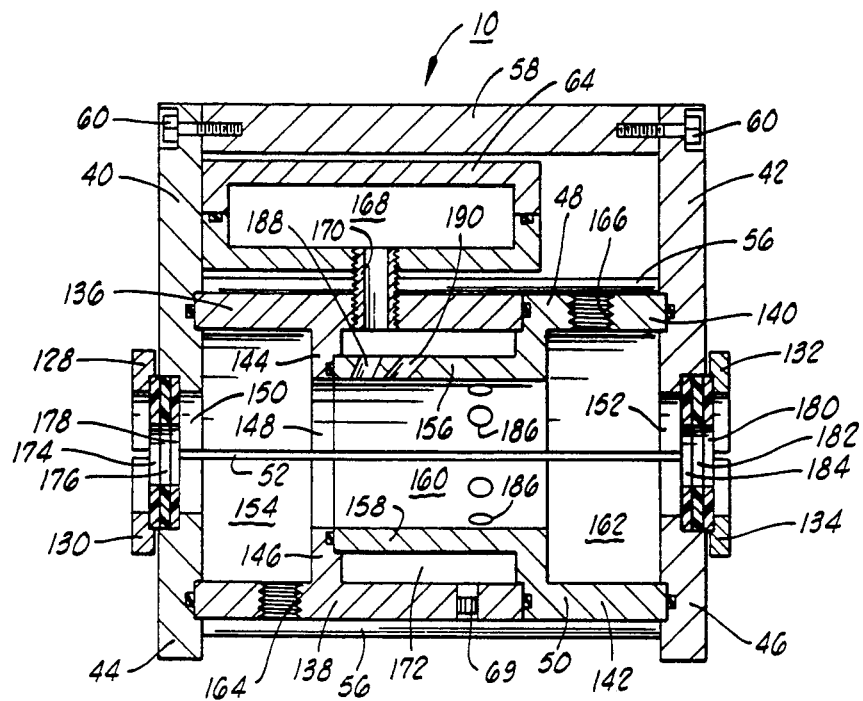
FIG. 4 is a vertical cross section taken longitudinally through the inspection chamber of the monitoring head.

As shown in FIG. 1, a tubing inspection head 10 of the present invention is intended for use at a well site 12 having a well head 14 and wellbore 16. A semi-truck trailer 18 is outfitted with a reel 20 of steel tubing 22 as rotationally supported on a stand 24. The reel 20 may contain thousands of feet of continuous steel tubing carried for use variously on the coiled tubing service rig. The steel tubing may range from approximately 1" in diameter up to as much as 3" in diameter depending upon the service usage.

The inspection head 10 may be mounted under control of a hydraulic aligning cylinder 26 at the end of the level wind system 28 which maintains proper positioning and alignment of reeled tubing on the reel 20. The steel tubing 22 is passed through the inspection head 10 on to a gooseneck 30 having position controlled by a hydraulically directed boom 32. The gooseneck 30 then directs the steel tubing 22 over and downward through a tubing injector 34 and into the well head 14. Tubing injector 34 is a pipe gripping device that can be operated to move the steel tubing 22 either upward or downward relative to wellhead 14.

Referring to FIGS. 2 and 3, the inspection head 10 includes upper and lower body castings 36 and 38 joined with respective upper end plates 40 and 42 and lower end plates 44 and 46. Upper and lower body sections 48 and 50 are joined together with a central gasket or horizontal seal 52 therebetween by means of a plurality of vertical assembly bolts (not shown) disposed within each of the respective bolt clearances 54, as disposed on each side of inspection head 10. Horizontal assembly bolts 56 (three per side) are each double thread-end bolts which are secured through the opposite upper end plates 40 and 42 and lower end plates 44 and 46.

An adaptor plate 58 is secured between the tops of upper end plates 40 and 42 by means of a series of bolts 60. The bolts 60 and the bolts securing double thread-end rods 56 are countersunk and thus not apparent on the FIG. 2 illustration. Likewise, bolts 62 are countersunk within upper end plate 40 as they secure an electronic housing 64 beneath adaptor plate 58. The electronic housing 64 is a sealed enclosure and includes a purge gas connection 66 connected to nitrogen source 67, a power connection 68 and a coaxial cable connector 70. Purge gas relief is via a bottom relief valve 69, as will be described in conjunction with FIG. 4. A lower pipe connector 72 provides fluid couplant input from couplant source 73 to the inner extremities of inspection head 10 while a similar pipe connector 74 provides fluid couplant output and return to source 73.

Inspection head 10 also includes opposite end roller assemblies 76 and 78 which function to properly align and feedthrough the steel tubing 22. The roller assembly 76 (see also FIG. 3) includes upper and lower calibration plates 80 and 82 which rigidly support respective pairs of roller brackets 84, 86 and 88, 90. Each of brackets 84 and 86 are formed with a counterbore to receive respective ones of bearing mounts 92 having eccentric counterbores for receiving a bearing 94. An axle 96 connected within bearing 94 carries a plastic roller 98 for contacting steel tubing 22.

In like manner, the lower bracket 90 is similarly constructed with bearing mount 100 carrying eccentric-mounted bearing 102 that provides rotational support for lower axle 104 and roller 106. The opposite end roller assembly 78 is also constructed with upper and lower calibration plates 108 and 110 supporting pairs of brackets 112 and 114 in support of respective bearing mounts 116 and 118 carrying eccentrically located bearings 120 and 122 which support upper and lower axles 124, 126 and their respective plastic rollers (not shown). The calibration method and structure of the roller assemblies is further discussed below.

Semi-circular seal caps 128 and 130 house a multi-ply rubber seal, to be further described, at one end of inspection head 10 while similar semi-circular seal caps 132 and 134 function at the opposite end. The semi-circular nature of the structure of inspection head 10 enables the device to be inserted into inspection attitude at any point along steel tubing 22 and not necessarily a starting end. Thus, by disengaging the plurality of vertical assembly bolts on each side of body sections 48 and 50, i.e., through bolt clearances 54, the upper and lower body sections 48 and 50 can be taken totally apart and inserted over and under the steel tubing 22 for reassembly in surround or inspection position. The seal caps 128, 130 and 132, 134 also separate semi-circularly to allow the installation, and the rubber seals are formed as discontinuous, round sections capable of being inserted over the steel tubing 22 during installation, as will be further described.

Referring to FIG. 4, the upper and lower body sections 48 and 50 are comprised of upper and lower housing members 136 and 138 coactively assembled with upper and lower array housings 140 and 142. Each of housing members 136 and 138 includes an inner, annular shoulder 144 and 146 defining a central bore 148 in axial alignment with a bore 150 in end plate 40 and with a bore 152 in end plate 42. An enlarged void space 154 is created between central bores 148 and 150. The upper and lower array housing members 140 and 142 comprise a cylindrical formation that is reduced to a lesser diameter upper and lower insert sections 156 and 158 that define a cylindrical, axial passage 160 concentric to bore wall 148. The passage 160 expands into a larger diameter void 162 adjacent the axial bore 152 leading out of inspection head 10.

In the particular mode of construction, O-ring type seals are employed at the abutting ends of the upper and lower body sections 48 and 50 as they are retained in clamped affixture between opposite end frames 40 and 42. Similarly, abutment type O-rings are employed between adjoining surfaces of housings 136 and 138 as they are forcibly retained in longitudinal alignment relative to array housing sections 48 and 50.

A threaded hole 164 receives pipe fitting 72 (FIG. 2) for input of fluid couplant for circulation through void spaces 154, 160 and 162 and for exit through threaded hole 166 and pipe fitting 74 (FIG. 2). Nitrogen or other purge gas is circulated through interior 168 of electronic housing 64 and through a threaded nipple 170 into an annular void space 172 disposed between the inner wall of housing member 136 and the insert sleeve 156, 158 of array housing sections 140 and 142. The lower housing member 138 includes the purge gas relief valve 69 communicating with the lower part of void space 172.

Rubber seals 174, 176 and 178 are retained in overlay by seal caps 128 and 130 as they are tightly bolted onto the respective upper and lower end plates 40 and 44. In like manner, the opposite end includes rubber seals 180, 181 and 184 retained by upper and lower end caps 132 and 134 as bolted securely against respective upper and lower end plates 42 and 46.

The upper and lower array housings 140 and 142 provide seating for the variously arrayed acoustic transducers. The circumferal array of equal-spaced radially aligned holes 186 receive compressional wave acoustic transducers disposed in potted enclosure and radially directed normal to the axis of bore 160, the axial path of th tested steel tubing. The radially aligned transducers 186 test for diameter, wall thickness, and tubing ovality, as will be further described below. Two additional in-line transducers are disposed in holes 188 and 190 which are aligned at 70° and 55°, respectively, to the axis of bore 160. Transducers disposed in these positions are used to provide data relating to inner diameter anomalies and outer diameter anomalies, as will be further described in greater detail. Nitrogen or other purge gas is input to interior 168 of electronic housing 64 to circulate through threaded nipple 170 into the surround space 172 thereby to maintain an inert atmosphere around any electrical component or bare wire connection.

It should be understood that the radially aligned transducers 168 may be disposed within a plane intersecting the axis of insert sections 156, 158 at other than a right angle. This angle of intersection may necessarily be changed due to the fact that couplant fluid does not continually envelop the test tubing at all radial points. Thus, the angle of intersection may be altered for different operating attitudes in accordance with the level sought by the couplant fluid within the interior chamber or voids 154, 160 and 162.

Figure 5:
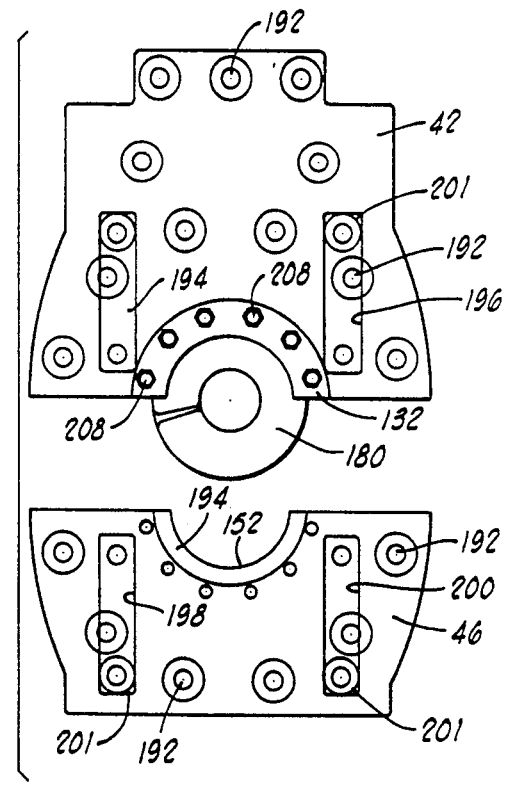
FIG. 5 is an end view in elevation and exploded form showing the upper and lower end plates of the inspection chamber with end seals partially exposed.

Referring to FIG. 5, the upper and lower end plates 42 and 46 are shown in exploded form in association with the respective seal and end cap structure. It should be understood that the opposite end plates 40 and 44 would be identical. Thus, the upper and lower end plates 42 and 46 each include a number of bolt holes for coaction with the horizontal assembly bolts 56, adaptor plate assembly bolts 60 and the like. Such bolt holes are designated generally as 192. The inspection bore 152 is formed with an annular shoulder counterbore 194 formed therearound, both upper and lower arcuate configurations, and shoulder 194 receives the three rubber seals 180, 182 and 184 therein in overlaid or stacked disposition. Thereafter, the seal cap 134 (see also FIG. 6) would be bolted onto lower end frame 46 with end plates 42 and 46 closed together when properly assembled. Also formed in upper and lower end plates 42 and 46 are $\frac{1}{8}$ inch deep indentations 194, 196, 198 and 200 which serve to seat the calibrating assemblies for the related roller assemblies, as will be further described.

Figure 6:
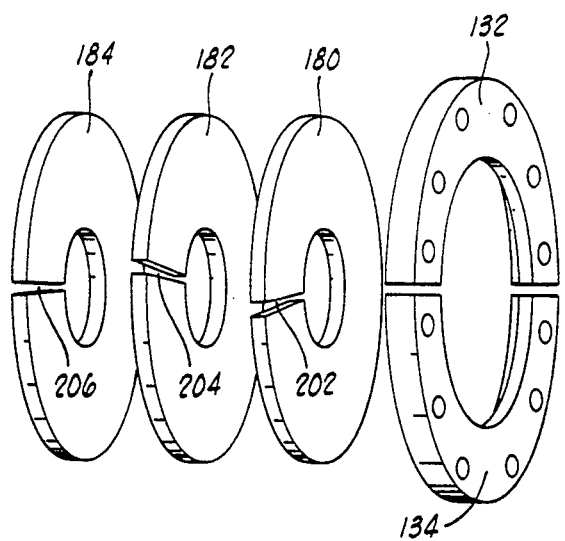
FIG. 6 is a perspective view in exploded form of the end seal structure.

FIG. 6 illustrates the rubber seals as they are split in off-line relationship to allow the steel tubing 22 to be slid sideways into the inspection bore when inspection head 10 is disassembled and placed on the steel tubing for initial positioning. It can be noted that rubber seals 180, 182 and 184 each have slits 202, 204 and 206 at different radial angles so that the steel tubing 22 can be forced into the axis with replacement of end cap 134 and tightening of bolts 208 and realignment and tightening of vertical assembly bolts to secure the upper and lower housing members 48 and 50. The seal assembly would be the same for each end of the inspection head 10 as the elastomer seals are formed from Buna N rubber material of about $\frac{1}{4}$ inch thickness.

Figure 7:
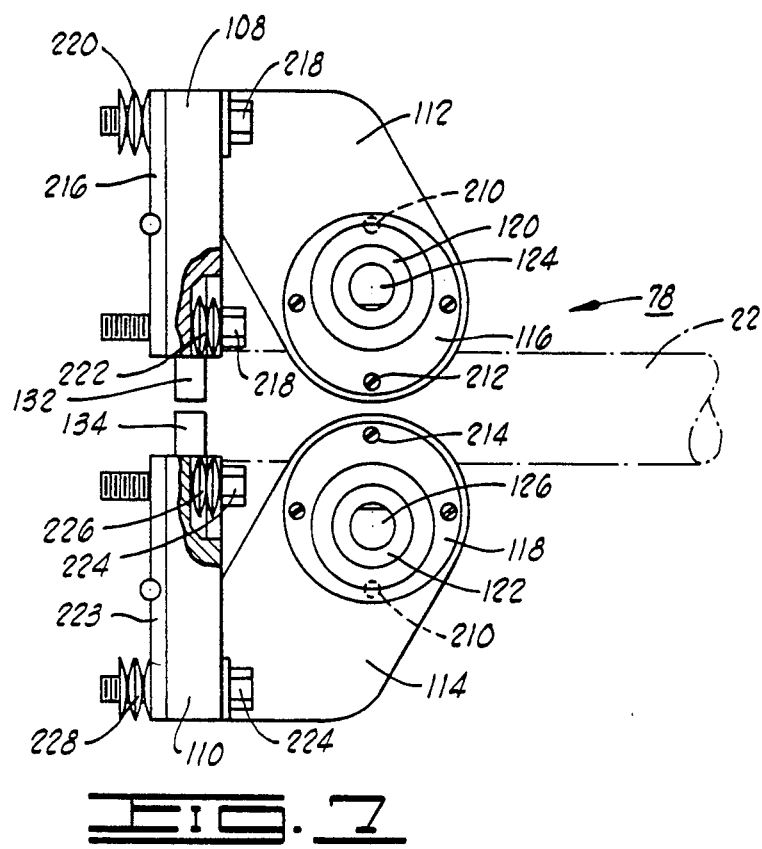
FIG. 7 is a side view in elevation of a roller bracket assembly of the present invention.

FIG. 7 illustrates the roller assembly 78, roller assembly 76 being identical. Each of the brackets 112, 114 includes four threaded holes 210 for receiving selectively three screws 212, 214 which function to position and retain the bearing mounts 116 and 118. The quadrature-arrayed threaded holes 210 enable the bearing mounts 116 and 118 to be shifted in 90° increments thereby to change the size of roller opening. That is, assuming that screws 212 and 214 as shown positioned in FIG. 7 place the eccentric bearings 120 and 122 at their furthest spacing, the roller assembly 78 is then in readiness to accept 1½ inch steel tubing. Then by shifting bearing mounts 116 and 118 by 90°, i.e., mount 118 clockwise and mount 116 counterclockwise, the rollers will be positioned to accept 1¼ inch steel tubing. Finally, if bearing mounts 116 and 118 are again shifted by 90° in the same directions of rotation, then the roller assembly 78 will be adjusted to receive one inch steel tubing.

Due to bending of the steel tubing during usage, the coiled tubing tends to attain a permanent radiused "set" wherein the radius will vary and present varying dimensions to the roller assembly as it accepts the steel tubing. To accommodate such smaller variations, each of the upper brackets 112 as retained on bracket plate 108 which rides upon a rocker plate 216 positioned within indentations 194, 196 (FIG. 5) as secured by retainer bolts 218. Upper retainer bolts 218 include four stacked Belleville washers 220 which are positioned within recesses 201 (FIG. 5) and the lower bolts 218 include a similar stack of Belleville washers 222 which are retained in a recess within the bracket plate 108. The similar tensioning arrangement applies for the lower bracket plate 110 riding on rocker plate 223 as upper bolts 224 retain the recessed stack of Belleville washers while lower bolts 224 function through a stack of Belleville washers 228 that are recessed within recess 201 of the lower end frame 46 (FIG. 5). Thus, the spring clearance allowed by the stacks of Belleville washers is sufficient to allow a radius swelled section of steel tubing to pass through the spaced rollers of roller assembly 78. Adequate safety factor to prevent destruction of the rollers is provided by off-setting the fulcrum point on the roller assemblies and by inserting a 0.187 inch wall nylon bushing around each of the mounting bolts 218, 224.

Figure 8:
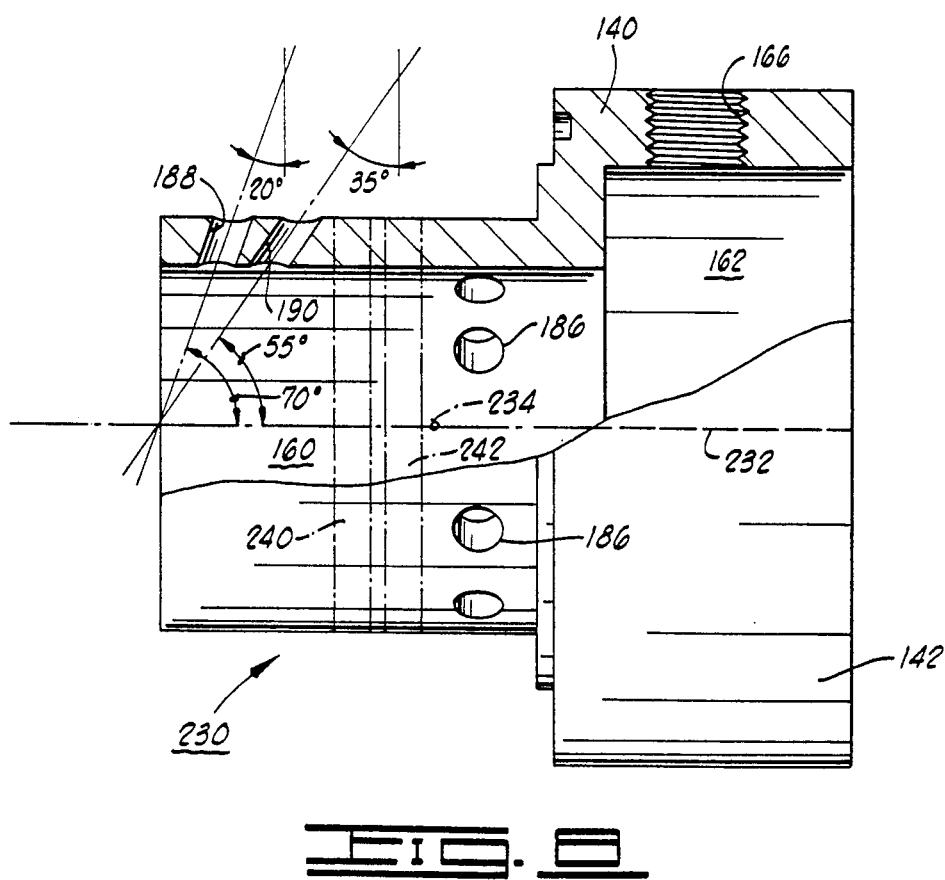
FIG. 8 is a partial vertical section of an alternative form of array housing used in the present invention.

Referring to FIG. 8, the basic array housing is shown as it is susceptible of a number of variations. The basic array housing 230 is utilized as a unitary part formation in one alternative embodiment of the invention. That is, the array housing is not divided along dash-line 232 into upper and lower half units as previously utilized in the embodiment where inspection head 10 is horizontally split and can be assembled around the steel tubing 22 with sealing about horizontal seal 52 (see FIG. 4). In an alternative form of the invention, array head 230 is a continuous body of revolution as is housing member 136, 138 about the central axis 234. When the inspection head is formed as a total volume of revolution without horizontal seam, the inspection head will not have the total versatility of inspection head 10 but there are appreciable reductions in the sealing problems.

The basic inspection head 10 utilizes eight or more equally spaced circumferal acoustic transducers radially aligned and normal to or at a selected angle to horizontal axis 234; and, in addition, the in-line transducers were placed in bores 188 and 190 at 70° and 55°, respectively, to the axis 234. The radial transducers in bores 186 are triggered to emit compressional wave energy which travels directly through the wall of steel tubing 22 to emit pulse indications each time it passes through and reflects through an interface so that the thinnest and thickest walls of the steel tubing 22 are detected. By an averaging process the major and minor axes of the various radial transducer returns are established and from this a measure of ovality or ellipticalness of the tubing can be indicated. Some of the acoustic energy arrives at a point of tangency on the coiled tubing and a portion of this energy is reflected from the inside wall of the tubing back through the outside wall and detected so that a measurement can be derived for the time of flight between the outside and inside wall of the tubing. Processing with a numerical constant then enables derivation of the wall thickness of the coiled tubing. Actually, the eight radial transducers in bores 186 emanating compressional wave energy may be used to establish any or all of the minimum remaining wall thickness, the ovality of the tubing and the average diameter of the tubing.

A transducer in the bore 190 disposed at 55° to the axis 234 emanates shear wave energy but responds to a modified Lamb wave to derive an indication of outer surface pitting. The pitting condition is general)y about the total circumference and a single transducer is effective. Another transducer operating through bore 188 at 70° to internal axis 234 is gated to measure inside diameter pitting, and here again the pitting condition is such that a single transducer is sufficient coverage. All of the transducers utilized are a commercially available type of Lead Metaniobate crystal that may be utilized variously as a compressional wave or shear wave generator, depending upon the position of excitation and crystal alignment. The Lead Metaniobate crystals are excited to produce output of 8.5 megahertz, as will be further described.

The above-described crystal array with approximately eight radial transducers and two in-line angular transducers is sufficient for obtaining all useful information relative to the monitoring mode of operation wherein the inspection head is utilized for testing at well-site location. However, for a certification procedure or an inspection of new or reconditioned tubing in a pipe yard, it may be desirable to test for still additional flaws, e.g., longitudinal flaws and transverse flaws. Thus, additional circumferal arrays of transducers, on the order of sixteen equal spaced transducers may be arrayed around the areas indicated by dash lines 240 and 242. In this case, transducer alignment and data processing may be carried out in accordance with the teachings of U.S. Pat. Nos. 4,404,853 and 4,541,064. Longitudinal tubing flaws may be detected by transducers around the band 240 as directed into the tubing member at an angle of about 25° from the direct radial, and transverse flaws may be detected with transducers in band 242 that are directed at about 25° from normal and transverse to the coiled tubing. Signal processing may be carried out in known manner as taught by the previous patents.

Figure 9:
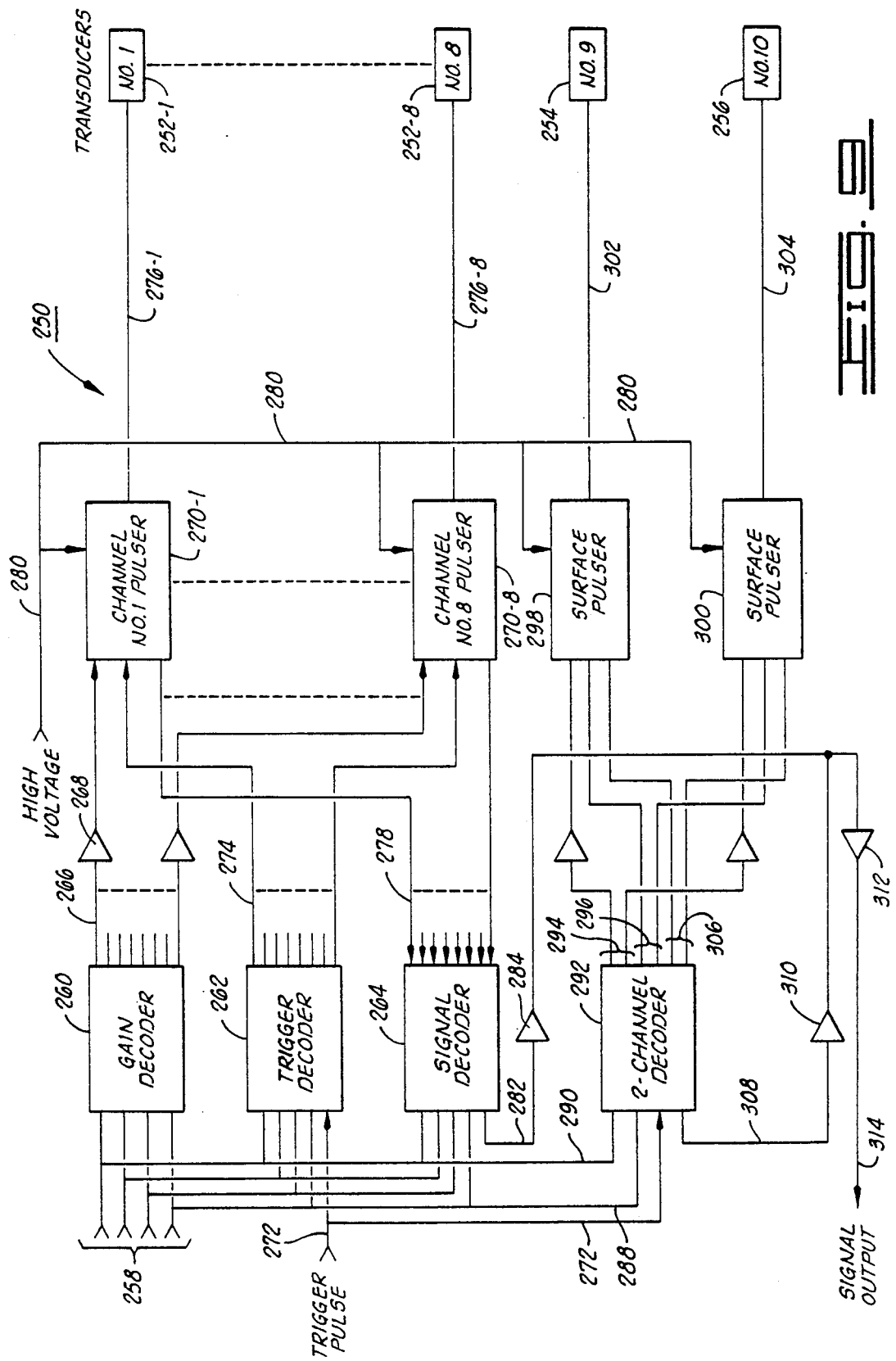
FIG. 9 is a block diagram of the pulser and receiving circuitry of the present invention.

Referring now to FIG. 9, a pulser and decoding circuit 250 provides immediate control of the radial transducers 252-1 through 252-8 as aligned in bores 186 (see FIG. 8), and the in-line transducers 254 and 256 as disposed in angle bores 188 and 190, respectively. Sequence control of the channel 1-8 transducers 252-1 through 252-8 is in the form of a four bit digital input 258 as derived from gate control circuitry to be further described. The four bit data input is then applied to each of a gain decoder 260, a trigger decoder 262 and a signal decoder 264. The gain decoder 260, an IC Type 4052, provides outputs via eight leads 266 and respective gain adjust amplifiers 268 for input to each of the channel pulsers 270-1 through 270-8. A trigger pulse input 272 is applied to trigger decoder 262 (IC Type 4052) which also receives the four bit control data on lead group 258 to produce output on leads 274 for input to each of the channel pulsers 270-1 through 270-8 that apply trigger to fire the respective transducers 252-1 through 252-8. Received signals from the same transducers are then conducted on connections 276-1 through 276-8 back through respective pre-amplifiers in the pulser circuits 270-1 through 270-8 for ultimate input to signal decoder 264 which is also under control of the four bit data group 258.

Each of the channel pulser circuits 270-1 through 270-8 is more properly termed a pulser decode circuit, an IC Type IRFF 311, which includes not only a high voltage FET which is triggered to provide firing voltage on leads 276-1 through 276-8, but also gain control circuitry, and a line driver for providing RF output on the leads 278 to signal decoder 264. High voltage on the order of 300 volts is applied on input lead 280 for application to all pulser circuits, i.e., channels 1-8 and also the two surface pulsers as will be further discussed. The RF output through signal decoder 264 (IC Type 4051) is then applied on line 282 through an inverter 284 and it is available at a junction 286.

A selected two bits of the lead group 258 are applied on leads 5 288 and 290 for input to a two channel decoder 292, IC Type 4053. Trigger signal on lead 272 is also applied to the two channel decoder 292 which provides outputs in the form of gain control outputs on leads 294, and trigger signal output on leads 296 to each of the surface pulsers 298 and 300. The surface pulsers 298, 300 in turn provide pulsing output on leads 302 and 304 to the inline transducers 254 and 256, and returned signal indication is reconducted back along lines 302 and 304 to the surface pulser line amplifier circuitry for output via leads 306 and RF signal input to decoder 292. The RF signals are then output on lead 308, amplified in amplifier 310 and conducted to junction point 286 where they are mixed with the radial signals for processing through amplifier 312 to signal output 314.

Figure 10:
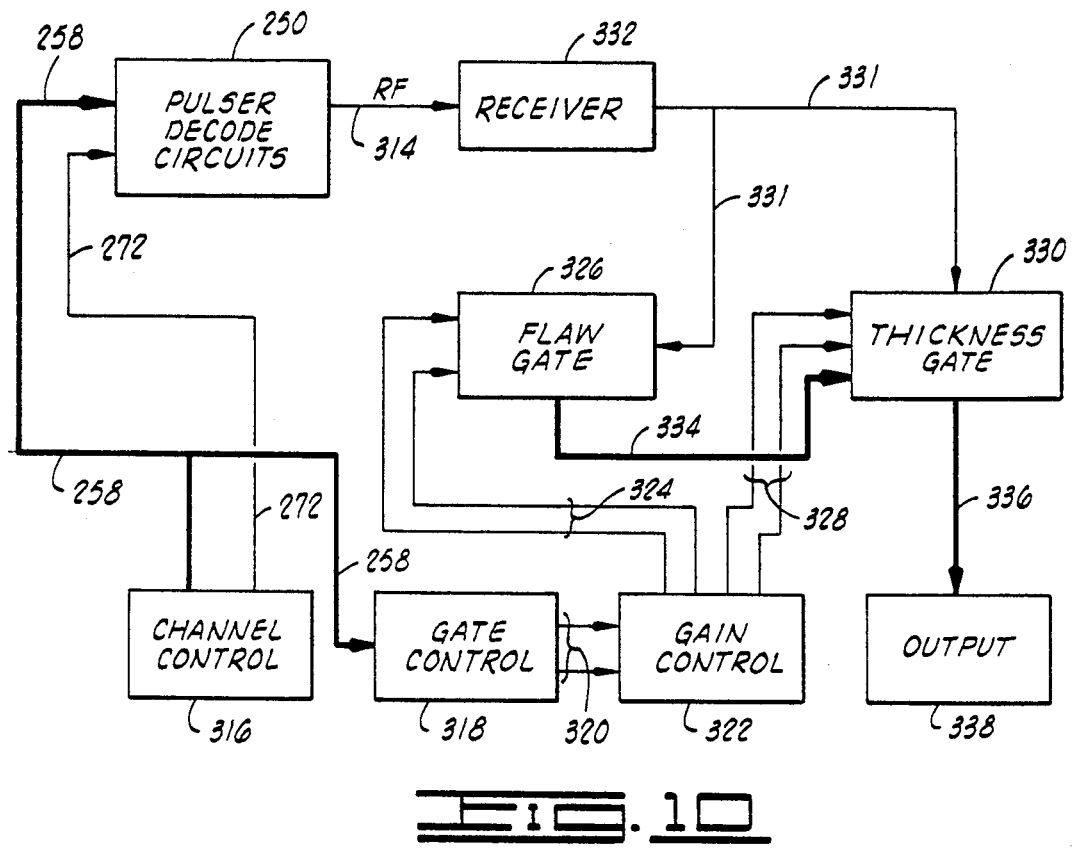
FIG. 10 is a system block diagram.

Referring to FIG. 10, the block diagram shows the circuit stages that are ancillary to the pulser decode circuits 250 as shown in FIG. 9. A channel control circuit 316 generates four bit data on lead group 258 which functions to sequence the various operations for firing and receiving return signal of the eight radial transducers and two in-line transducers (see FIG. 9). Channel control circuit 316 also generates the trigger signal which is present on lead 272 to the pulser decode circuits 250. The four bit data lead group 258 is also applied to a gate control circuit 318 which generates the starting and ending gate pulses at predetermined spacing and duration. The start and end gate pulses on lead pair 320 are then applied to a gain control stage 322 which further generates flaw start and end gate pulses on lead pair 324 for input to a flaw gate 326. Gain control 322 also generates thickness start and end gate pulses on lead pair 328 for input to a thickness gate 330.

A receiver 332 receives the RF signal output on lead 314 from pulser decode circuits 250 in demodulated form, a video-type signal, for input on lead 331 to each of flaw gate 326 and thickness gate 330. Counting and processing circuitry within the flaw gate 326 then develops the flaw signal as an eight bit digital signal on lead group 334 for input to thickness gate circuit 330. At this stage, thickness gate data is added to the digital data on lead group 334 and eight bit data output is present on lead group 336 to output 338. The output data on lead group 336 is then in condition for application to a standard type of computer such as a Winn AT computer or a user's own customized computer. The digital output on lead group 336 can also be utilized by such as recorders, graphic analyzers, etc.

Figure 11:
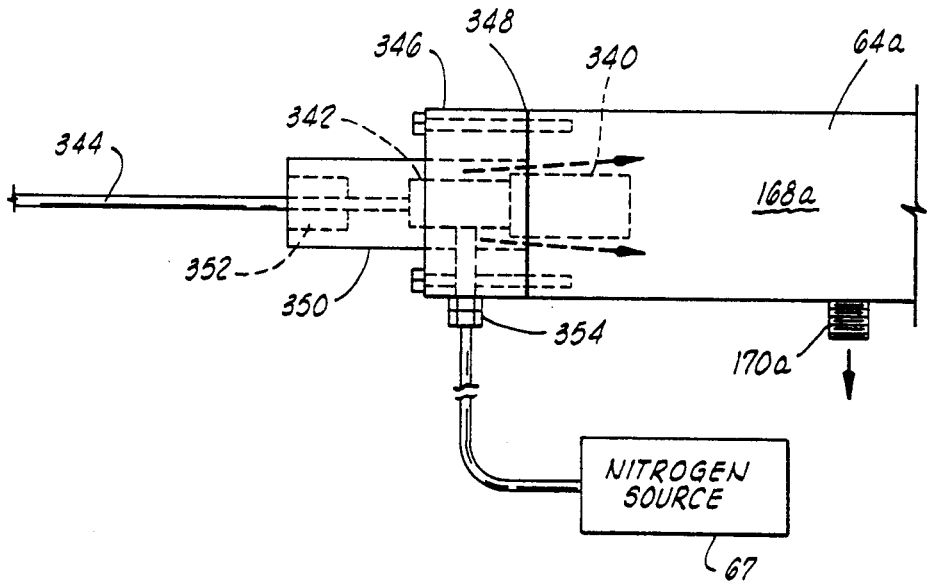
FIG. 11 is an idealized view of an electronic control box and cable connector that enables total gas purging of all circuitry.

FIG. 11 illustrates the purge gas connection that is suitable for certification testing of the unit in accordance with oil industry standards. All electrical connections, including plug connectors are maintained in a purge gas inert atmosphere, e.g., Nitrogen. The electronics housing 64a is fitted with a single multi-plug male connector 340 which conducts the multiple power control lines 276x, 302 and 304 as well as two coaxial signal connections and the power connection. A mating female connector 342 and multi-conductor cable 344 lead from the operating position.

A receptacle enclosure 346 is bolted onto housing 64a in sealed envelopment of female connector 340. A seal is disposed around the edge 348 of enclosure 346. An enclosure sleeve 350 is slidably retained on cable 344 with a compressible, elastomer annular seal 352 retained therein. The sleeve 350 is received within enclosure 346 in sealed, threaded engagement with annular seal 352 isolating the exterior. A feed-through nipple 354 is formed to permit Nitrogen flow at selected pressure from Nitrogen source 67 through receptacle enclosure 346, surrounding connectors 340, 342, and then through the interior 168a of housing 64a and out through nipple 170a to the transducer surround space 172 (see FIG. 4) for release at relief valve 69. Thus, all electronic connections, including plug connections, can be initially purged and then maintained under selected inert gas pressure.

In operation, the inspection head may take the shape of either an inspection head 10 (FIG. 2) which may be horizontally split into two sections, thus enabling the inspection head 10 to be assembled around a line of coiled tubing wherever it is situated; or, an alternative inspection head device that has no horizontal separation and is formed from a generally cylindrical configuration such that coiled tubing or other tubing under test must be inserted through one end seal and through the head interior for exit at the other end seal in order to prepare the unit for operation. It should also be understood that the inspection head assemblies may be utilized in or around the pipe yard for certification inspection of steel tubing, production tubing or other tubular goods; or, the inspection head 10 can be used in the monitoring mode with operational steel tubing as is shown in FIG. 1 where inspection head 10 is connected adjacent the tubing reel and level-wind mechanism and directing steel tubing onto the gooseneck and down into a well bore.

When assembling the two piece model of the equipment, inspection head 10, the top and bottom sections 36 and 38, are positioned with the top section on the coiled tubing 22 between the reel 20 and gooseneck 30 using the four corner vertical assembly bolts loosely engaged in clearances 54 to stabilize the assembly. The three split rubber seals (FIG. 6) may be inserted around the coiled tubing with splits rotated one from the other in sufficient spacing, three rubber seals at each side of inspection head 10, and then snugly secured within the bore provided in the respective upper and lower end plates 40, 44 and 42, 46. Thereafter, the additional vertical assembly screws may be inserted and tightened, and the split end caps 128, 130 and 132, 134 may be bolted on the end plates in capture of the respective 3-ring seals. When the end caps are properly positioned, the three thick rubber disks will be compressed to 0.625 inches thereby to insure a water tight seal about the coiled tubing. Also, in this attitude the properly selected roller assemblies will be in proper alignment contact with the coiled tubing 22.

Next, the 10 pin electrical cable (not shown) can be connected to the back of connector 70 of the electronic housing 64 and the coaxial cable can be connected to the coax connector 70 at electronic housing 64. Nitrogen pressure hose from a suitable nitrogen source 67 or other purging gas can be connected at hose fitting 66. The nitrogen line should be applied through purging and allowed to maintain a pressure of about 2 psi. Couplant input from a source 73 may be applied through pipe fitting 72 and suitable pump pressure will allow couplant circulation with return flow from pipe fitting 74 back to couplant source 73, a suitable pump/reservoir packet. The monitor head assembly should now be operational and it may be controlled by the unit operator and/or a computer under control of selected software program. The inspection head 10 contains eight radially aligned ultrasonic transducers functioning at 8.5 megahertz and these transducers 252-1 through 252-8 (see FIG. 9) are energized by a high voltage pulse at the rate of 600 pulses per second. From these transducers the thinnest remaining wall and the shape of the tube or the ovality is defined 600 times per second. An additional two in-line, angularly oriented surface transducers 254 and 256 are operated for the purpose of detecting inside diameter and outside diameter transverse and longitudinal anomalies in the tube wall as well as to define the surface condition of the tubing, i.e., pit-corrosion. In a pre-set duration, all of the transducers are interrogated within a selected gated position. The time/distance between two, or more of the voltage outputs that occur within the gate are interrogated to determine the actual wall thickness of the tube at a specific time and place. The control electronics recognize threshold values of acceptable tube conditions that permit a wide range of GO-NO-GO decisions that may be made without operator intervention. Any deviations in wall thickness and/or out-of-tolerance pipe shapes that exceed a preset threshold range will activate an alarm, i.e. both visual and audible alarm.

The foregoing discloses a novel form of ultrasonic testing device for tubular goods, particularly coiled tubing, which enables detection, recognition and recording of tubing factors such as ovality, inside and outside diameter pitting conditions, remaining diameter, remaining wall thickness, transverse flaws and longitudinal flaws. The present system operates under highly automated control with the ability to recognize the various flaws and the degrees of such flaws whereupon a linear record of tubing condition may be kept.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. Apparatus for testing of continuous tubing at a well site adjacent to a well bore, comprising:
    an elongate housing securely supported between a source of continuous tubing and the well bore to receive the tubing therethrough;
    first and second resilient sealing means secured on opposite ends of said elongate housing and each receiving said continuous tubing therethrough in sealed manner;
    an acoustic energy test array having generally cylindrical form being disposed in alignment between said first and second resilient sealing means to receive the continuous tubing axially;
    plural, equi-spaced, circumferentially placed acoustic energy sensors disposed in radial alignment around said test array and being operative for determining the degree of ovality of said continuous tubing;
    compartmentation means within said elongate housing having couplant fluid input and output and extending through said test array and between said first and second resilient sealing means to surround said continuous tubing; and
    couplant fluid continually flowing through said compartmentation means.

2. Apparatus as set forth in claim which is further characterized to include:

a second acoustic energy sensor disposed in said test array as directed radially but at a longitudinal angle of approximately 55° to the axis of said test array for determining pitting of an outside surface of said continuous tubing.

3. Apparatus as set forth in claim which is further characterized to include:

a third acoustic energy sensor disposed in said test array as directed radially but at a longitudinal angle of approximately 70° to the axis of said test array for determining pitting of an inside surface of said continuous tubing.

4. Apparatus as set forth in claim 2 which is further characterized to include:

a third acoustic energy sensor disposed in said test array as directed radially but at a longitudinal angle of approximately 70° to the axis of said test array for determining pitting of an inside surface of said continuous tubing.

5. Apparatus as set forth in claim 1 which is further characterized to include:

an air-tight electronic housing having a communication conduit connected to said elongate housing;

a second compartmentation means within said elongate housing in communication with said conduit and enveloping each of said acoustic energy sensors; and purging means for circulating non-combustible gas through said electronic housing and the second compartmentation means including all electrical connectors.

6. Apparatus as set forth in claim 5 which is further characterized to include:

a plurality of pulser/pre-amp circuits mounted in said electronic housing and connected through said conduit to a respective one of said plurality of acoustic sensors.

7. Apparatus as set forth in claim 5 wherein said first and second resilient sealing means each comprise:

plural, elastomeric discs having a round central hole that when under compression is slightly smaller in diameter than said continuous tubing.

8. Apparatus as set forth in claim which is further characterized to include:

first and second pairs of spaced rollers each mounted adjacent the respective first and second sealing means in contact with and directing said continuous tubing.

9. Apparatus as set forth in claim 7 which is further characterized to include:

first and second pairs of spaced rollers each mounted adjacent the respective first and second sealing means in contact with and directing said continuous tubing.

10. Apparatus as set forth in claim 4 which is further characterized to include:

first and second pairs of spaced rollers each mounted adjacent the respective first and second sealing means in contact with and directing said continuous tubing.

11. Apparatus as set forth in claim 8 which is further characterized to include:

first and second eccentric bushings rotatably supporting said first and second pairs of spaced rollers.

12. Apparatus as set forth in claim 5 which is further characterized to include:

a multi-conductor cable having a first multi-contact connector;

a second multi-contact connector at said electronic housing for mating engagement with the first multi-contact connector; and a receptacle enclosure sealingly secured to said electronic housing to enclose said first and second multi-contact connectors and maintain sealed within the circulating non-combustible gas.

13. Apparatus for on-site testing of continuous tubing when fed from a spool source to a well bore, comprising:

a housing assembly adapted for enclosure around said continuous tubing;

first and second resilient seals disposed on opposite sides of said housing assembly and in alignment to receive the continuous tubing therethrough;

fluid-tight first compartmentation means enveloping said continuous tubing and extending between said seals, a portion of said first compartmentation means being formed as a generally cylindrical test array frame disposed coaxially with said continuous tubing passing therethrough;

a plurality of acoustic sensors seated about the circumference of said test array frame and directed in radial alignment toward said continuous tubing;

a fluid couplant maintained within said first compartmentation means;

a plurality of pulser-preamp circuits connected to control respective acoustic sensors and provide a signal output; and means for processing the signal output and determining the degree of ovality of said continuous tubing.

14. Apparatus as set forth in claim 13 which is further characterized to include:

first and second pairs of rollers affixed adjacent said respective first and second resilient seals to receive said continuous tubing in firm roller contact therethrough.

15. Apparatus as set forth in claim 13 which is further characterized to include:

a shear wave acoustic sensor means seated in said test array frame to provide indication of pitting along an outside surface of the continuous tubing.

16. Apparatus as set forth in claim 13 which is further characterized to include:

a Lamb wave acoustic sensor means seated in said test array frame to provide indication of pitting along an inside surface of the continuous tubing.

17. Apparatus as set forth in claim 13 wherein said resilient seals each comprise:

plural plys of radially slit, elastomer seal rings secured in overlay and defining a central hole that is slightly less in diameter than said continuous tubing.

18. Apparatus as set forth in claim 17 which further comprises:

a compressor ring for closing the slit in said elastomer seal rings.

19. Apparatus as set forth in claim 13 wherein said housing assembly further comprises:

an upper half housing having a joinder surface bisecting first and second passages for receiving said seals;

a lower half housing having a joinder surface bisecting first and second passages for receiving said seals;

a sealing gasket for disposal between said upper half housing and lower half housing; and means for rigidly securing the upper and lower half housings.

20. Apparatus as set forth in claim 19 wherein said resilient seals each comprise:

plural plys of elastomer seal rings secured in overlay and defining a central hole that is slightly less in diameter than said continuous tubing, each of said plys being split radially at a selected position.

21. Apparatus as set forth in claim 13 wherein said test array frame comprises:

a cylinder portion of selected diameter to receive continuous tubing therethrough;

a collar portion formed on one end of said cylinder portion coaxial therewith;

a plurality of equi-spaced, circumferal holes formed around the circumference of said cylinder portion for receiving radially directed acoustic sensors; and first and second holes formed in the cylinder portion disposed in-line and directed radially but at longitudinal angles to the axis of the cylinder portion of 70° and 55° respectively, said holes receiving first and second acoustic sensors.

22. Apparatus as set forth in claim 21 wherein:

said radially directed acoustic sensors disposed in said circumferal holes each transmit a compressional wave; and said first and second acoustic sensors disposed in said first and second holes each transmit shear waves.

23. A method for testing of continuous tubing at a well bore, comprising the steps of:

intercepting the continuous tubing between a reel source and the point of entry into the well bore;

maintaining a fluid couplant envelope at said point of interception as said continuous tubing moves therethrough;

effecting plural acoustic sensor operation within said fluid couplant envelope to determine any variations between orthogonal diameters of said tubing; and indicating said variations between orthogonal diameters as a degree of ovality of said tubing.

24. A method as set forth in claim 23 which is further characterized by steps of:

effecting a second acoustic sensor operation within said fluid couplant to determine and indicate any pitting of an outside surface of the tubing.

25. A method as set forth in claim 23 which is further characterized by steps of:

effecting another acoustic sensor operation within said fluid couplant to determine and indicate any pitting along an inside surface of the tubing.

26. A method as set forth in claim 24 which is further characterized by steps of:

effecting a third acoustic sensor operation within said fluid couplant to determine and indicate any pitting along an inside diameter surface of the tubing.

27. A method as set forth in claim 23 wherein:

said plural acoustic sensor operation includes transmission of compression waves.

28. A method as set forth in claim 24 wherein:

said second acoustic sensor operation includes transmission of shear waves.

29. A method as set forth in claim 25 wherein:

said third acoustic sensor operation includes generation and detection of Lamb waves.

30. A method as set forth in claim 28 wherein:

said third acoustic sensor operation includes generation and detection of Lamb waves.

31. A method as set forth in claim 23 which is further characterized by the step of:

maintaining at said point of interception an envelope of Nitrogen in surround of all electronics components and electrical connections.

* * * * *

UNITED STATES PATENT AND TRADEMARK OFFICE
CERTIFICATE OF CORRECTION

Patent No.: 5,303,592

Dated: April 19, 1994

Inventor(s): Waylon A. Livingston

It is certified that error appears in the above-identified patent and that said Letters Patent is hereby corrected as shown below:

Column 4, line 55, delete "th" and insert --the-- therefor;

Column 7, line 2, delete "general)y" and insert --generally-- therefor;

Column 8, line 8, delete the numeral "5" between "leads" and "288";

Column 11, line 1, insert --1-- between "claim" and "which";

Column 11, line 8, insert --1-- between "claim" and "which"; and

Column 11, line 45, insert --1-- between "claim" and "which".

Signed and Sealed this

Ninth Day of August, 1994

BRUCE LEHMAN

*Attest:*

*Attesting Officer*    *Commissioner of Patents and Trademarks*